US011259779B2

(12) United States Patent
Arai

(10) Patent No.: US 11,259,779 B2
(45) Date of Patent: Mar. 1, 2022

(54) ULTRASOUND BODY TISSUE DETECTING DEVICE, ULTRASOUND BODY TISSUE DETECTING METHOD, AND ULTRASOUND BODY TISSUE DETECTING PROGRAM

(71) Applicant: FURUNO ELECTRIC CO., LTD., Nishinomiya (JP)

(72) Inventor: Tatsuo Arai, Takarazuka (JP)

(73) Assignee: Furuno Electric Co., Ltd., Nishinomiya (JP)

(*) Notice: Subject to any disclaimer, the term of this patent is extended or adjusted under 35 U.S.C. 154(b) by 309 days.

(21) Appl. No.: 15/539,604

(22) PCT Filed: Nov. 26, 2015

(86) PCT No.: PCT/JP2015/083155
§ 371 (c)(1),
(2) Date: Jun. 23, 2017

(87) PCT Pub. No.: WO2016/104034
PCT Pub. Date: Jun. 30, 2016

(65) Prior Publication Data
US 2018/0333137 A1    Nov. 22, 2018

(30) Foreign Application Priority Data

Dec. 26, 2014 (JP) .............................. JP2014-265167

(51) Int. Cl.
*A61B 8/00* (2006.01)
*A61B 8/14* (2006.01)
(Continued)

(52) U.S. Cl.
CPC ................. *A61B 8/46* (2013.01); *A61B 8/14* (2013.01); *G01S 7/52036* (2013.01);
(Continued)

(58) Field of Classification Search
CPC ..... A61B 8/5207; A61B 8/5223; A61B 8/085; A61B 8/14; A61B 8/46; A61B 8/0858; G01S 15/8977; G01S 7/52036
See application file for complete search history.

(56) References Cited

U.S. PATENT DOCUMENTS 4,780,831 A    10/1988 Iwata et al.
5,111,823 A *  5/1992 Cohen ................. G01S 7/52028
                                                    600/443
(Continued)

FOREIGN PATENT DOCUMENTS

CN    103037771 A    4/2013
JP    H 61-40678 A   2/1986
(Continued)

OTHER PUBLICATIONS

Ng, J. et al. "Automatic Measurement of Human Subcutaneous Fat with Ultrasound". IEEE Transactions on Ultrasonics, Ferroelectrics, and Frequency Control, vol. 56, No. 8, Aug. 2009 (p. 1642-1653) (Year: 2009).*

(Continued)

*Primary Examiner* — Keith M Raymond
*Assistant Examiner* — Milton Truong
(74) *Attorney, Agent, or Firm* — Knobbe, Martens, Olson & Bear, LLP

(57) ABSTRACT

A body tissue to be detected is automatically detected certainly with high precision. An ultrasonic body tissue detecting device may include a transmission/reception unit, a two-dimensional data acquisition unit, a spatial frequency distribution calculation unit and a determination unit. The transmission/reception unit may transmit an ultrasonic signal into a body of a sample and receive an echo signal of the ultrasonic signal. The two-dimensional data acquisition unit may form two-dimensional echo image in a transmitting direction of the ultrasonic signal and in a scanning direction.

(Continued)

The spatial frequency distribution calculation unit may perform a spatial frequency conversion of the two-dimensional echo image and calculate a spatial frequency distribution for a determining position. The determination unit may determine whether the determining position is the body tissue to be detected based on a distribution of amplitude in the transmitting direction of the ultrasonic signal and a distribution of amplitude in the scanning direction of the spatial frequency distribution.

14 Claims, 7 Drawing Sheets

(51) Int. Cl.
    *G06T 1/00* (2006.01)
    *G01S 15/89* (2006.01)
    *G01S 7/52* (2006.01)
    *A61B 5/00* (2006.01)
    *A61B 8/08* (2006.01)

(52) U.S. Cl.
    CPC ............ *G01S 15/8915* (2013.01); *G06T 1/00* (2013.01); *A61B 5/6828* (2013.01); *A61B 8/085* (2013.01); *A61B 8/5207* (2013.01); *A61B 8/5223* (2013.01); *G01S 15/8977* (2013.01)

(56) References Cited

U.S. PATENT DOCUMENTS

| | | | |
|---|---|---|---|
| 8,858,446 B2 | 10/2014 | Sato | |
| 9,192,354 B2 | 11/2015 | Takagi et al. | |
| 9,498,189 B2 | 11/2016 | Taniguchi et al. | |
| 2003/0149357 A1* | 8/2003 | Liu | G01S 7/52028 600/437 |
| 2005/0070795 A1 | 3/2005 | Karasawa | |
| 2006/0184023 A1* | 8/2006 | Satoh | A61B 8/14 600/437 |
| 2011/0077519 A1 | 3/2011 | Katsuyama | |
| 2013/0046175 A1 | 2/2013 | Sumi | |
| 2013/0066210 A1* | 3/2013 | Sumi | G01S 7/52038 600/447 |
| 2014/0064591 A1* | 3/2014 | Sasaki | A61B 8/00 382/131 |
| 2015/0057543 A1* | 2/2015 | Katsuyama | A61B 8/4488 600/438 |
| 2015/0221092 A1* | 8/2015 | Mega | G06T 7/42 382/103 |

FOREIGN PATENT DOCUMENTS

| | | |
|---|---|---|
| JP | 2007-301035 A | 11/2007 |
| JP | 2010-094422 A | 4/2010 |
| JP | 2011-092686 A | 5/2011 |
| JP | 2014-033914 A | 2/2014 |

OTHER PUBLICATIONS

Sikdar et al. "Dynamic Ultrasound Imaging Applications to Quantify Musculoskeletal Function". Exerc Sport Sci Rev. Jul. 2014 ; 42(3): 126-135 (Year: 2014).*

Bashford, G.R. "Tendinopathy Discrimination by Use of Spatial Frequency Parameters in Ultrasound B-Mode Images". IEEE Transactions on Medical Imaging, vol. 27, No. 5, 2008 (Year: 2008).*

Ng, J., et al., "Automatic Measurement of Human Subcutaneous Fat with Ultrasound", IEEE Transactions on Ultrasounds, Ferroelectrics and Frequency Control, IEEE, vol. 56, No. 8, Aug. 1, 2009, pp. 1642-1653.

Extended Search Report in PCT Application No. PCT/JP2015/083155 dated Sep. 11, 2018, 9 pgs.

International Search Report dated Feb. 23, 2016 in PCT Application No. PCT/JP2015/083155, 6pgs.

* cited by examiner

ULTRASOUND BODY TISSUE DETECTING DEVICE, ULTRASOUND BODY TISSUE DETECTING METHOD, AND ULTRASOUND BODY TISSUE DETECTING PROGRAM

CROSS REFERENCE TO RELATED APPLICATIONS

This application is a U.S. National stage of International Application No. PCT/JP2015/083155 filed on Nov. 26, 2015. This application claims priority to Japanese Patent Application No. 2014-265167 filed on Dec. 26, 2014. The entire disclosure of Japanese Patent Application No. 2014-265167 is hereby incorporated herein by reference.

TECHNICAL FIELD

The present disclosure relates to an ultrasonic body tissue detecting device which transmits an ultrasonic wave into a body and detects target body tissue based on an echo signal of the ultrasonic wave.

BACKGROUND ART

Conventionally, various ultrasonic diagnosing devices are devised, as disclosed in Patent Document 1. Such ultrasonic diagnosing devices transmit ultrasonic signals into a body from outside and generate image data to determine a state inside the body based on echo signals of the ultrasonic signals.

Specifically, the ultrasonic diagnosing device transmits the ultrasonic signal in a direction perpendicular to the surface of skin using a probe for transmitting and receiving the ultrasonic wave. The ultrasonic diagnosing device then receives the echo signal which is acquired by the ultrasonic signal reflecting on body tissue. The ultrasonic diagnosing device moves the position of the ultrasonic probe along the skin surface and receives the echo signal at a plurality of positions. Thus, the ultrasonic diagnosing device forms a two-dimensional echo image in a depth direction parallel to the transmitting direction of the ultrasonic signals and in a scanning direction parallel to the skin surface. For example, the ultrasonic diagnosing device sets a higher luminosity at a position where amplitude of the echo signal is larger and sets a lower luminosity at a position where the amplitude of the echo signal is smaller to form the two-dimensional echo image which expresses the amplitudes of the echo signals by the luminosities.

Such a two-dimensional echo image is utilizable for processing which detects given body tissue. For example, it is utilizable for processing to detect muscular tissue at a part of the surface of a femur where muscular tissue, subcutaneous tissue, and skin exist in layers.

Conventionally, in order to distinguish the muscular tissue from the subcutaneous tissue, an operator observes the pattern of a luminosity distribution of the two-dimensional echo image displayed on a display unit, etc. The operator grasps beforehand the differences between a luminosity distribution pattern of the subcutaneous tissue and a luminosity distribution pattern of the muscular tissue. The operator then distinguishes the muscular tissue from the subcutaneous tissue based on the luminosity distribution patterns. Further, the operator determines that a position where the luminosity distribution pattern changes is a boundary (fascia) between the subcutaneous tissue and the muscular tissue.

REFERENCE DOCUMENT OF CONVENTIONAL ART

Patent Document

[Patent Document 1] JP2011-092686A

DESCRIPTION OF THE DISCLOSURE

Problems to be Solved by the Disclosure

However, according to the method of observing the two-dimensional echo image by the operator and distinguishing the muscular tissue from the subcutaneous tissue described above, the detection accuracy of the muscular tissue is dependent on the experiences of the operator.

Moreover, the amplitude of the echo signal (the luminosity of the echo image) for the muscular tissue varies with aging and, thus, the difference between the luminosity distribution patterns of the subcutaneous tissue and the muscular tissue varies according to the age of person of interest for the detection.

Thus, the conventional method of observing the two-dimensional echo image and detecting the muscular tissue by the operator is to manually detect the muscular tissue, and it is not easy to detect the muscular tissue securely with high precision. Similarly, when detecting the subcutaneous tissue, the distinction from the muscular tissue is not easy.

Therefore, the purpose of the present disclosure is to provide an ultrasonic body tissue detecting device, a method of ultrasonically detecting body tissue, and an ultrasonic body tissue detecting program, which automatically detect body tissue to be detected certainly with high precision.

SUMMARY OF THE DISCLOSURE

An ultrasonic body tissue detecting device according to one aspect of the present disclosure, may include a transmission/reception unit, a two-dimensional data acquisition unit, a spatial frequency distribution calculation unit, and a determination unit. The transmission/reception unit may transmit an ultrasonic signal into a body of a sample and receive an echo signal of the ultrasonic signal. The two-dimensional data acquisition unit may acquire two-dimensional data in a transmitting direction of the ultrasonic signal and in a scanning direction substantially perpendicular to the transmitting direction of the ultrasonic signal, based on the echo signals acquired at a plurality of positions along the surface of the sample. The spatial frequency distribution calculation unit may perform a spatial frequency conversion of the two-dimensional data, two-dimensionally into a depth direction defined by the transmitting direction of the ultrasonic signal and into a horizontal direction perpendicular to the depth direction, and calculate a spatial frequency distribution for a determining position. The determination unit may determine whether the determining position is given body tissue based on a distribution of a frequency component in the depth direction and a distribution of a frequency component in the horizontal direction of the spatial frequency distribution.

With this configuration, a difference between the spatial frequency distribution of given body tissue and the spatial frequency distribution of the other body tissue which is adjacent to the given body tissue may be obtained in numeric values. Therefore, by evaluating the numeric values, whether the determining position is the given body tissue may be determined so as to detect the given body tissue.

In addition, in the ultrasonic body tissue detecting device of this aspect of this disclosure, the determination unit may determine based on a difference between the frequency components at two points of which a spatial frequency in the depth direction is identical to a spatial frequency in the horizontal direction in the spatial frequency distribution.

In addition, in the ultrasonic body tissue detecting device of this aspect of this disclosure, the determination unit may determine based on an integrated value obtained by integrating the difference between the frequency components at the two points in the depth direction and the horizontal direction.

In addition, in the ultrasonic body tissue detecting device of thia aspect of this disclosure, the determination unit may determine based on a result of comparison of the integrated value with a given threshold.

In these configurations, a concrete model to determine the given body tissue is described, and by using these configuration, the given body tissue may be automatically detectable certainly with high precision.

In addition, in the ultrasonic body tissue detecting device of this aspect of this disclosure, the given body tissue may be muscular tissue. The determination unit may determine that the determining position is the muscular tissue if the integrated value is above the threshold.

With this configuration, the muscular tissue may be automatically detectable as the given body tissue certainly with high precision.

In addition, in the ultrasonic body tissue detecting device of this aspect of this disclosure, the determination unit may detect an angle difference between the transmitting direction of the ultrasonic signal and the depth direction using the spatial frequency distribution. The determination unit may calculate a distribution of frequency component in the depth direction and a distribution of frequency component in the horizontal direction based on the angle difference.

With this configuration, even if the transmitting direction of the ultrasonic signal is not parallel to the depth direction, the given body tissue may be automatically detectable certainly with high precision.

Effect of the Disclosure

According to the present disclosure, the body tissue to be detected, such as the muscular tissue and the subcutaneous tissue, may automatically be detected certainly with high precision.

MODES FOR CARRYING OUT THE DISCLOSURE

Figure 1:
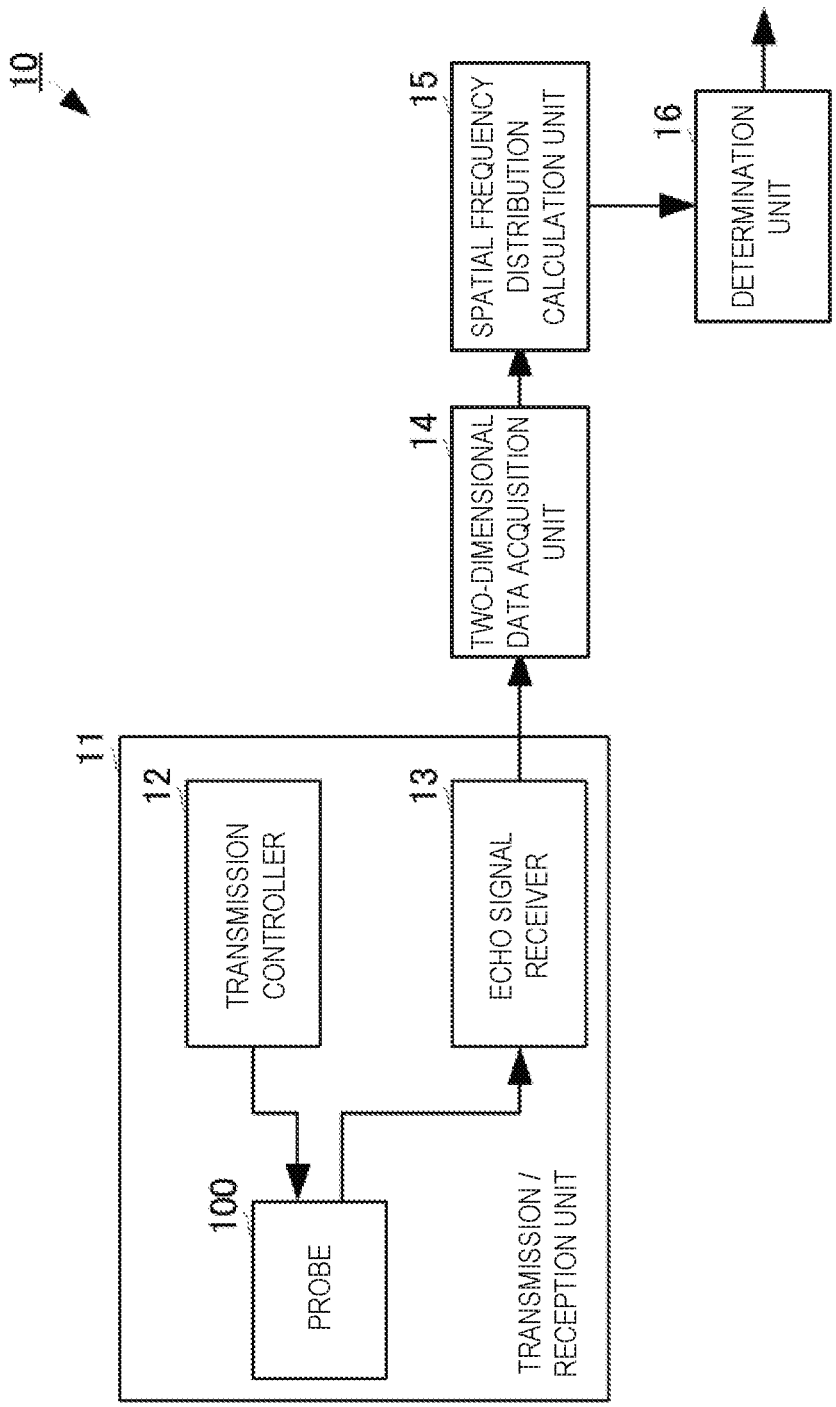
FIG. 1 is a configuration view of an ultrasonic body tissue detecting device according to a first embodiment of the present disclosure.

An ultrasonic body tissue detecting device, a method of ultrasonically detecting body tissue, and an ultrasonic body tissue detecting program according to a first embodiment of the present disclosure are described with reference to the accompanying drawings. FIG. 1 is a configuration view of the ultrasonic body tissue detecting device according to the first embodiment of the present disclosure.

An ultrasonic body tissue detecting device 10 may include a transmission/reception unit 11, a two-dimensional data acquisition unit 14, a spatial frequency distribution calculation unit 15, and a determination unit 16. The transmission/reception unit 11 may include a transmission controller 12, an echo signal receiver 13, and a probe 100.

The transmission controller 12 may generate a transmission control signal which is obtained by shaping a carrier wave at a frequency within an ultrasonic range into a pulse shape. The transmission controller 12 may output the transmission control signal to the probe 100.

The probe 100 may include, for example, a linearly-arrayed ultrasonic transducer comprised of a plurality of elements. The ultrasonic transducer may be excited by the transmission control signal and transmit an ultrasonic signal to the outside (into a body of a sample). Here, the ultrasonic transducer may have its axis in a direction (a transmitting direction of the ultrasonic signal) perpendicular to a transmission/reception surface of the probe 100, and transmit the ultrasonic signal comprised of a given transmission beam angle.

The transmission/reception surface of the probe 100 may contact a skin surface in parallel to the skin surface of the sample. Thus, the ultrasonic signal transmitted from the ultrasonic transducer may be propagated inside the sample in a direction (a depth direction) substantially perpendicular to the skin surface. That is, the transmitting direction of the ultrasonic signal may be identical to the depth direction.

The ultrasonic signal may be reflected on each body tissue inside the sample. Specifically, at a position where muscular tissue, subcutaneous tissue, and skin cover the surface of a femur in this order, the ultrasonic signal reflects on the skin, the subcutaneous tissue, the muscular tissue, and the surface of the femur. The echo signal caused by this reflection may be propagated inside the sample in a direction parallel to the transmitting direction of the ultrasonic signal, and then received by the ultrasonic transducer.

The probe 100 may be disposed so as to be able to scan in a direction parallel to the skin surface of the sample. The probe 100 may transmit the ultrasonic signal from the ultrasonic transducer and receive the echo signal at a plurality of positions in the scanning direction. The probe 100 may output the echo signal received by the ultrasonic transducer to the two-dimensional data acquisition unit 14.

The two-dimensional data acquisition unit 14 may acquire two-dimensional data based on the echo signals acquired from the plurality of positions on the skin by the probe 100. The two-dimensional data acquisition unit 14 may form a two-dimensional echo image using the two-dimensional data. Specifically, the two-dimensional data acquisition unit 14 may detect an amplitude value of each echo signal at every sampling timing set with a given time interval. Thus, the two-dimensional data acquisition unit 14 may calculate the amplitude value of each echo signal at every sampling point of a plurality of sampling points which are located in the transmitting direction of the ultrasonic signal.

The two-dimensional data acquisition unit 14 may arrange the plurality of echo signals having the plurality of amplitude values in the scanning direction to obtain a distribution of the amplitude value comprised of a two-dimensional area in the transmitting direction and the scanning direction of the ultrasonic signal. Here, as illustrated in this embodiment, if the transmitting direction of the ultrasonic signal is perpendicular to the skin surface, the transmitting direction of the ultrasonic signal may be the depth direction and the scanning direction may be a horizontal direction which is a direction parallel to the skin. The two-dimensional data acquisition unit 14 may set luminosity according to the amplitude value to form the two-dimensional echo image.

Figure 2:
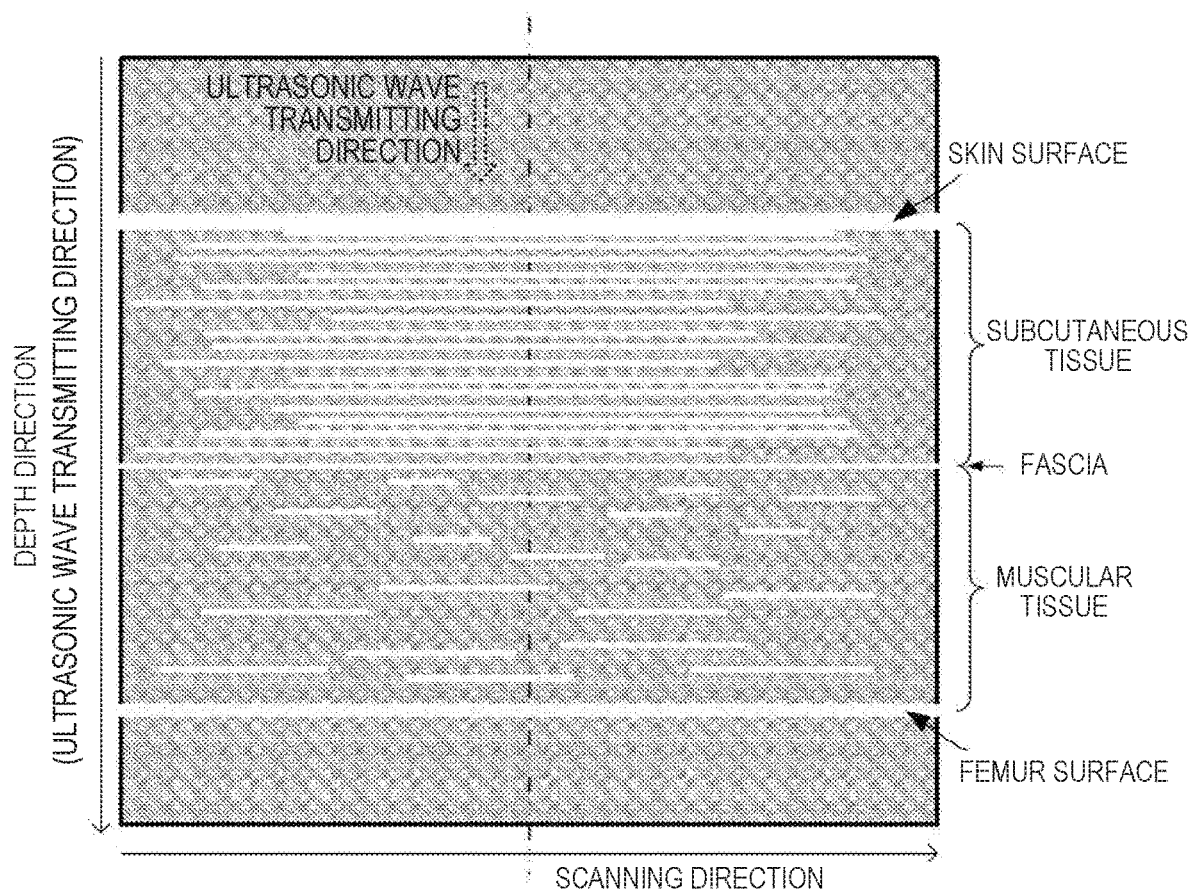
FIG. 2 is a view illustrating one example of a two-dimensional echo image which is formed by the ultrasonic body tissue detecting device according to the first embodiment of the present disclosure.

FIG. 2 is a view illustrating one example of the two-dimensional echo image which is formed by the ultrasonic body tissue detecting device according to the first embodiment of the present disclosure. Note that FIG. 2 is illustrated so that the luminosity is higher (whiter) as the amplitude increases, and the luminosity is lower (blacker) as the amplitude decreases.

As illustrated by the two-dimensional echo image data of FIG. 2, at the skin surface and at the femur surface, the luminosity may be higher (the amplitude of the echo signal increases). In addition, at the skin surface and at the femur surface, a high-luminosity line part extending in the scanning direction (i.e., a direction parallel to the skin surface) may appear, respectively. Each of the line parts caused by the skin surface and the femur surface may appear thickly (the length in the transmitting direction of the ultrasonic signal is long), without any break of the line part in the scanning direction.

As illustrated by the two-dimensional echo image data of FIG. 2, a plurality of high-luminosity line parts extending in the scanning direction may appear in subcutaneous tissue. These line parts may appear comparatively long in the scanning direction, but they may be shorter than the line parts caused by the skin surface and the femur surface. Moreover, these line parts may appear continuously at a certain interval in the transmitting direction (depth direction) of the ultrasonic signal.

As illustrated by the two-dimensional echo image data of FIG. 2, short line parts may appear in the muscular tissue, and they may tend to be lower in the luminosity for a youth but higher in the luminosity for an aged person. For this reason, if each body part is observed only by the overall luminosity, a relation between an average luminosity of the subcutaneous tissue and an average luminosity of the muscular tissue may be reversed between the youth and the aged person and, thus, the muscular tissue may not be distinguished from the subcutaneous tissue based on the averages of luminosities. Note that these line parts may be shorter than the line parts caused by the subcutaneous tissue. Moreover, these line parts may not always appear substantially at the same interval in the transmitting direction (depth direction) of the ultrasonic signal, but appear at a variable interval in general.

As illustrated by the two-dimensional echo image data of FIG. 2, the line parts having features similar to the skin surface and the femur surface may appear at a fascia, (i.e., the surface of the muscular tissue). However, the line part caused by the fascia may appear with a thickness substantially equal to the thickness of the line parts which appear in the subcutaneous tissue and the muscular tissue.

As described above, in the two-dimensional echo image (two-dimensional data), the subcutaneous tissue and the muscular tissue may have different features from the skin surface and the femur surface. Moreover, in the two-dimensional echo image, the subcutaneous tissue may have a different feature from the muscular tissue.

The spatial frequency distribution calculation unit 15 may calculate a spatial frequency distribution based on the two-dimensional data centering on a determining position. Specifically, the spatial frequency distribution calculation unit 15 may execute a two-dimensional spatial frequency conversion processing, which is defined by a frequency component "u" in the scanning direction (horizontal direction) and a frequency component "v" in the transmitting direction (depth direction) of the ultrasonic signal, based on the two-dimensional data (i.e., the two-dimensional distribution of the amplitude value of the plurality of echo signals).

Figure 3:
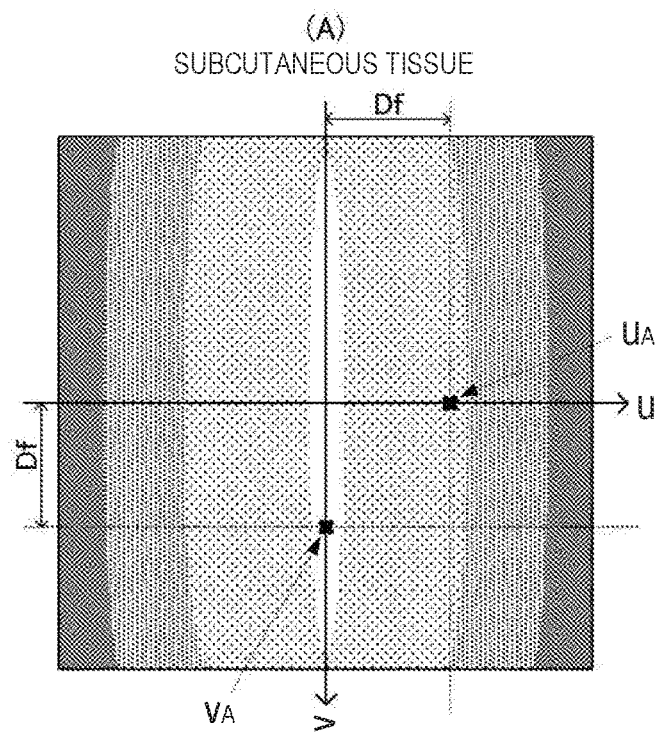
FIGS. 3(A) and 3(B) are views illustrating examples of a spatial frequency distribution which are calculated by the ultrasonic body tissue detecting device according to the first embodiment of the present disclosure.
Figure 3:
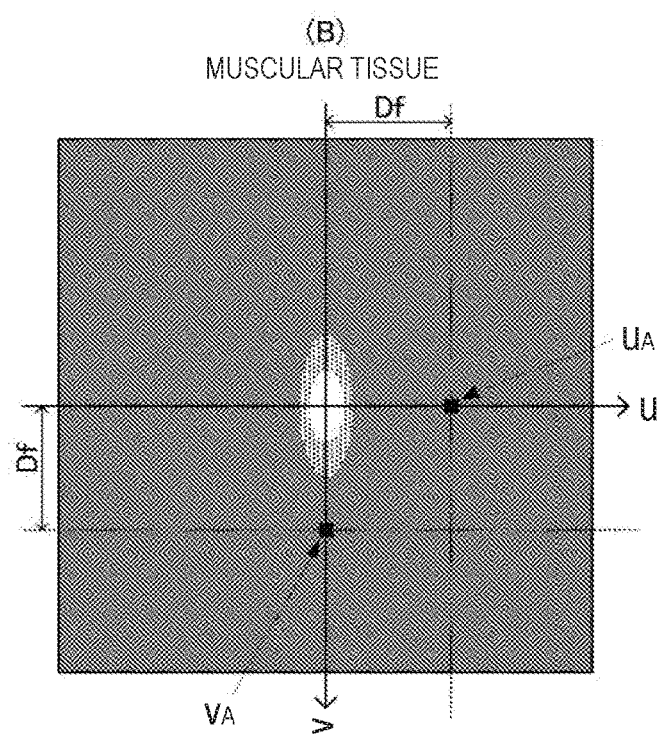

FIGS. 3A and 3B are views illustrating examples of the spatial frequency distribution calculated by the ultrasonic body tissue detecting device according to the first embodiment of the present disclosure. FIG. 3(A) illustrates a spatial frequency distribution of the subcutaneous tissue, and FIG. 3(B) illustrates a spatial frequency distribution of the muscular tissue.

As illustrated by the spatial frequency distribution of FIG. 3(A), in the subcutaneous tissue, an intensity value (value) of each frequency component (hereinafter, referred to as "the frequency component") may be higher in the transmitting direction (depth direction) of the ultrasonic signal, over a broad band of frequency from a Direct Current ("DC") component to a high-frequency component. This is due to that, as described above, in the subcutaneous tissue, the line part (a portion where the amplitude value of the echo signal is high) may appear continuously at a certain interval in the transmitting direction of the ultrasonic signal.

Moreover, as illustrated by the spatial frequency distribution of FIG. 3(A), in the subcutaneous tissue, the DC component may be higher in the scanning direction (horizontal direction), but other frequency components, especially high-frequency components may be lower. This is due to that, as described above, in the subcutaneous tissue, the line parts may extend in the scanning direction, and the line parts may not be repeated in the scanning direction. On the other hand, since the line parts may be clearly repeated in the depth direction, the high-frequency component in the transmitting direction (depth direction) of the ultrasonic signal may be larger.

As illustrated by the spatial frequency distribution of FIG. 3(B), in the muscular tissue, the DC component may be higher in both the transmitting direction (depth direction) and the scanning direction (horizontal direction) of the ultrasonic signal, but other frequency components, especially the high-frequency components may be lower.

This is due to that, as described above, in the muscular tissue, extending lengths of the line parts in the scanning direction may be shorter, and the plurality of line parts may not continuously appear repeatedly in the transmitting direction of the ultrasonic signal.

As described above, in the spatial frequency distribution, the subcutaneous tissue may have different features from the muscular tissue.

The spatial frequency distribution calculation unit 15 may calculate the spatial frequency distribution for every determining position, and then output them to the determination unit 16.

The determination unit 16 may acquire a frequency component characteristic (a v-direction frequency component characteristic) in the ultrasonic wave transmitting direction (depth direction) of the spatial frequency distribution, and a frequency component characteristic (a u-direction frequency component characteristic) in the scanning direction (horizontal direction) of the spatial frequency distribution. The v-direction frequency component characteristic may be expressed by a matrix of each frequency component in the ultrasonic wave transmitting direction centering on a reference point which is a point representing the DC component. The u-direction frequency component characteristic may be expressed by a matrix of each frequency component in the scanning direction centering on the reference point.

FIGS. 4(A) and 4(B) are views illustrating examples of the frequency component characteristic calculated by the ultrasonic body tissue detecting device according to the first embodiment of the present disclosure. FIG. 4(A) illustrates the frequency component characteristic of the subcutaneous tissue, and FIG. 4(B) illustrates the frequency component characteristic of the muscular tissue.

Figure 4:
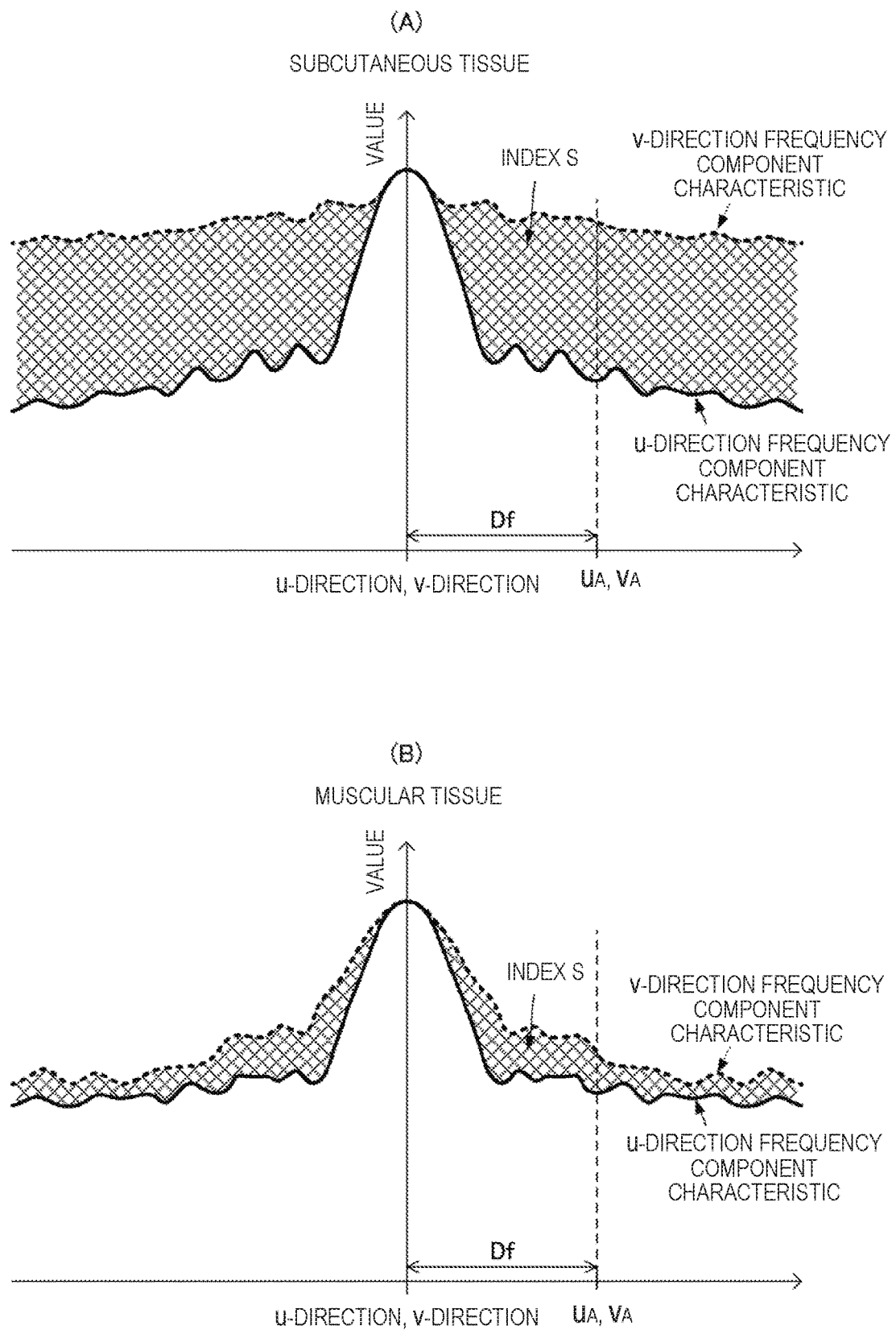
FIGS. 4(A) and 4(B) are views illustrating examples of a frequency component characteristic which are calculated by the ultrasonic body tissue detecting device according to the first embodiment of the present disclosure.

As illustrated by the frequency component characteristic of FIG. 4(A), each frequency component in the v-direction may be regularly higher in the subcutaneous tissue. Moreover, in the subcutaneous tissue, the DC component in the u-direction may be higher, but the frequency component may fall as the frequency becomes higher. For this reason, as for the frequency components away from the reference point in the v-direction and the u-direction by the same frequency distance Df (see FIGS. 3 and 4), the frequency component of the v-direction frequency component characteristic may be larger than the frequency component of the u-direction frequency component characteristic. The same can be said for almost all frequency components, except for those near the reference point. Therefore, a difference between the v-direction frequency component characteristic and the u-direction frequency component characteristic may be higher over a substantially entire band of frequency, except for the frequency components near the DC component.

As illustrated by the frequency component characteristic of FIG. 4(B), in the muscular tissue, the DC component may be high without depending on the v-direction and the u-direction, but the frequency component may fall as the frequency becomes higher. For this reason, as for the frequency components away from the reference point in the v-direction and the u-direction by the frequency distance Df (see FIGS. 3 and 4), the frequency component of the v-direction frequency component characteristic may substantially be identical to the frequency component of the u-direction frequency component characteristic. The same can be said for almost all frequency components including those near the reference point. Therefore, the difference between the v-direction frequency component characteristic and the u-direction frequency component characteristic may be smaller over the substantially entire band of frequency.

The determination unit 16 may determine whether the determining position is the subcutaneous tissue or the muscular tissue based on such a difference between the frequency component characteristic of the subcutaneous tissue and the frequency component characteristic of the muscular tissue. Alternatively, the determination unit 16 may determine whether the determining position is body tissue to be detected (e.g., the muscular tissue).

Specifically, the determination unit 16 may calculate a difference value between the frequency components at two points of which the spatial frequencies in the depth direction and the horizontal direction in the spatial frequency distribution are identical as described above (i.e., a difference value between the frequency components of the v-direction frequency component characteristic and the u-direction frequency component characteristic at the positions away from the reference point by the same frequency distance). The determination unit 16 may calculate this difference value for each frequency component obtained from the spatial frequency distribution. The determination unit 16 may integrate the difference values of the frequency components in the depth direction and the horizontal direction to calculate the integrated value as an index S.

The determination unit 16 may prestore a threshold Th of the index S. The threshold Th may be suitably set from arithmetic values which are acquired as an average value and a minimum value of the index S of the subcutaneous tissue, and an average value and a maximum value of the index S of the muscular tissue by experiments etc. conducted beforehand. For example, a mean value between the average value of the index S of the subcutaneous tissue and the average value of the index S of the muscular tissue may be set as the threshold Th.

The determination unit 16 may compare the index S with the threshold Th, and if the index S is above the threshold Th, it may determine that the determining position is the subcutaneous tissue. On the other hand, if the index S is below the threshold Th, the determination unit 16 may determine that the determining position is the muscular tissue.

The determination unit 16 may move the determining position in the transmitting direction (depth direction) of the ultrasonic signal, and determine whether it is the subcutaneous tissue or the muscular tissue for every determining position. Thus, a boundary (fascia) between the subcutaneous tissue and the muscular tissue may also be detectable for every transmission (every sweep) of the ultrasonic signal, and a range of the subcutaneous tissue (thickness) and a range of the muscular tissue (thickness) may also be detectable.

As described above, the muscular tissue and the subcutaneous tissue may be automatically detectable certainly with high precision by using the configuration of this embodiment. Note that in the embodiment described above, although the detection of the muscular tissue and the subcutaneous tissue may be described as the example, the body tissue to be detected may be automatically detectable certainly with high precision by using the configuration of this embodiment, if body tissue of which the spatial frequency distribution differs exists.

Figure 5:
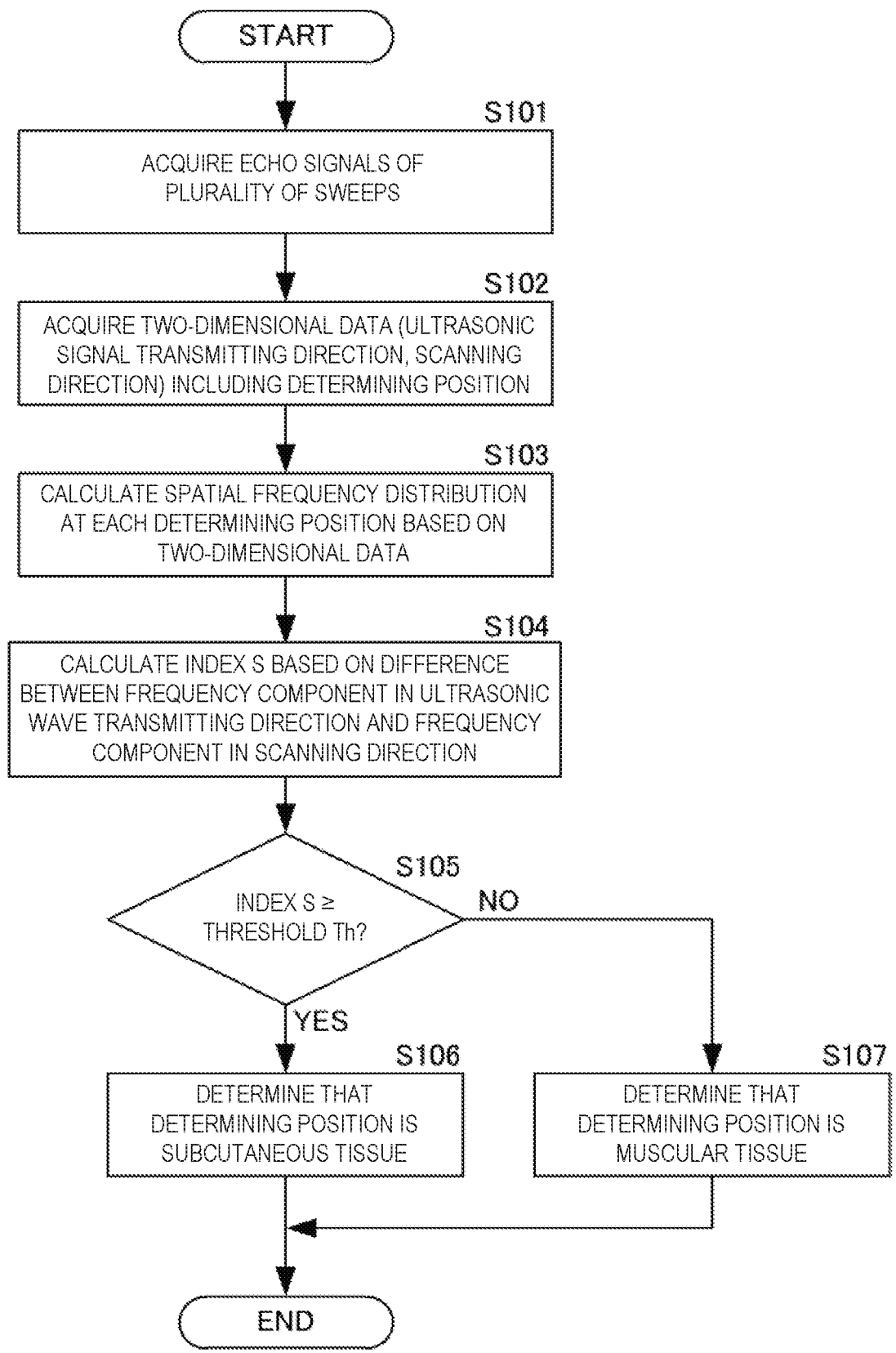
FIG. 5 is a flowchart illustrating a processing flow of a method of ultrasonically detecting body tissue according to the first embodiment of the present disclosure.

Note that although in the above description, a mode in which each processing may be implemented by an individual functional block, the detection processing of the body tissue by the ultrasonic signal may be programmed and stored, and an arithmetic processing device, such as a computer, may read out and execute the program. In this case, the following flow may be used. FIG. 5 is a flowchart illustrating a processing flow of a method of ultrasonically detecting the body tissue according to the first embodiment of the present disclosure.

The arithmetic processing device may transmit the ultrasonic signal at different positions, and acquire the echo signals. That is, the arithmetic processing device may acquire the echo signals of a plurality of sweeps (S101).

The arithmetic processing device may acquire the two-dimensional data including the determining position using the echo signals of the plurality of sweeps (S102).

The arithmetic processing device may calculate the spatial frequency distribution at the determining position based on the two-dimensional data (S103).

The arithmetic processing device may calculate the index S based on the difference between the frequency component in the ultrasonic wave transmitting direction (v-direction) and the frequency component in the scanning direction (u-direction) of the spatial frequency distribution (S104).

If the index S is above the threshold Th (S105: YES), the arithmetic processing device may determine that the determining position is the subcutaneous tissue (S106). If the index S is below the threshold Th (S105: NO), the arithmetic processing device may determine that the determining position is the muscular tissue (S107).

Next, an ultrasonic body tissue detecting device according to a second embodiment of the present disclosure is described with reference to the accompanying drawings. The ultrasonic body tissue detecting device according to this embodiment may be the same as the ultrasonic body tissue detecting device according to the first embodiment in the fundamental configurations and processings, and may be a device in which a function to correct an inclination (angle difference) of the ultrasonic wave transmitting direction with respect to the depth direction is added to the ultrasonic body tissue detecting device of the first embodiment.

When the probe 100 contacts the skin surface, the transmission/reception surface of the probe 100 may incline so that the depth direction inside the body may not be parallel to the transmitting direction of the ultrasonic signal (the angle difference is produced between the depth direction and the transmitting direction).

Figure 6:
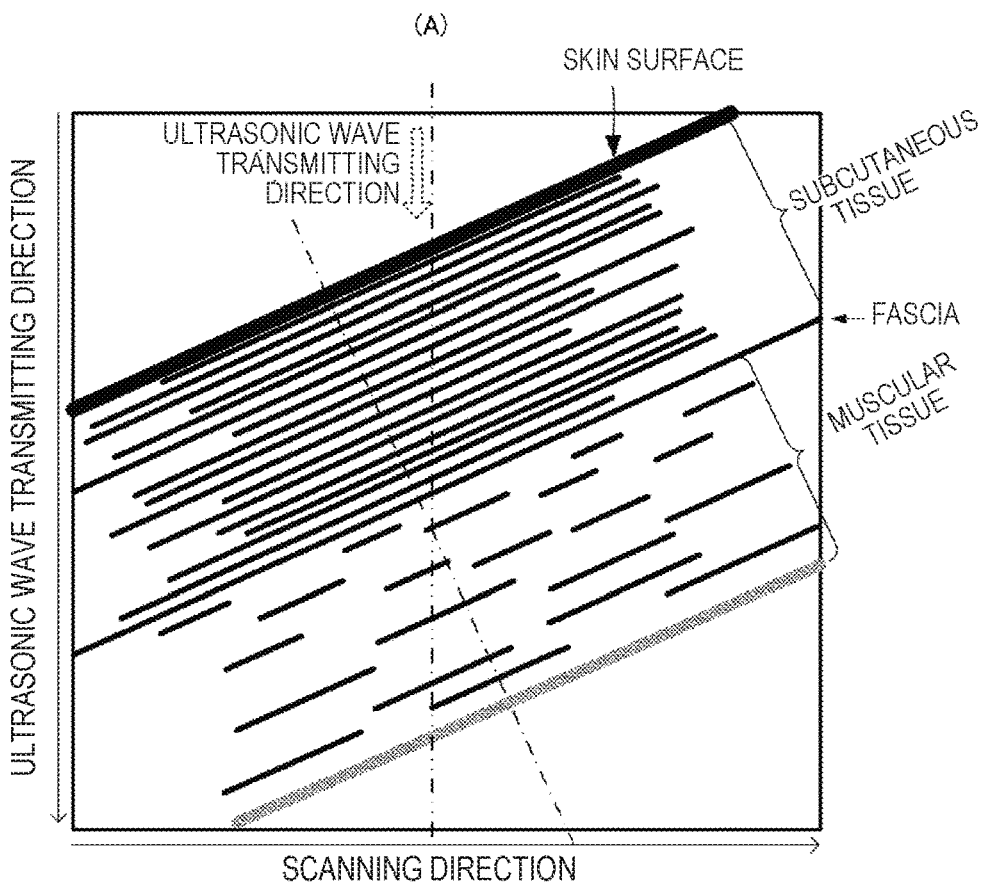
FIGS. 6(A) and 6(B) illustrate a view of a two-dimensional echo image and a view of a spatial frequency distribution of subcutaneous tissue, when a depth direction is not parallel to a transmitting direction of an ultrasonic signal.
Figure 6:
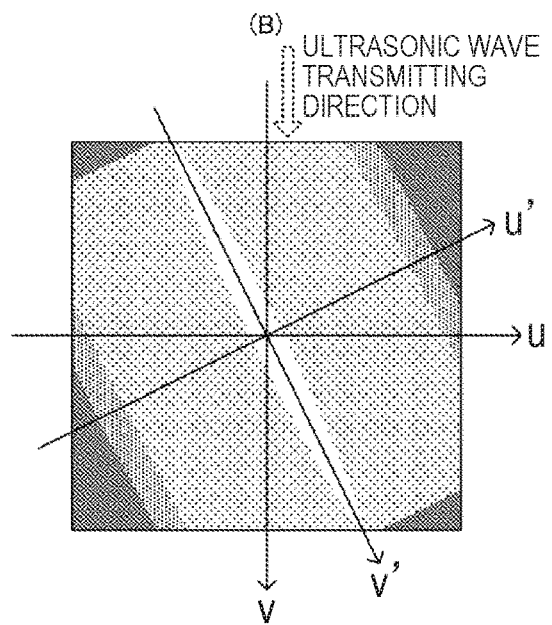

FIG. 6(A) is a view illustrating a two-dimensional echo image when the depth direction is not parallel to the ultrasonic wave transmitting direction, and FIG. 6(B) is a view illustrating a spatial frequency distribution of the subcutaneous tissue when the depth direction is not parallel to the ultrasonic wave transmitting direction.

In such a case, as illustrated in FIG. 6(A), the extending direction of the plurality of line parts in the subcutaneous tissue may not be parallel to the scanning direction, and the direction of the plurality of line parts arrayed at intervals may not be parallel to the transmitting direction of the ultrasonic signal.

Thus, as illustrated in FIG. 6(B), the arrayed direction of the high-frequency components in the spatial frequency distribution of the subcutaneous tissue may not be parallel to the ultrasonic wave transmitting direction.

As illustrated in FIG. 6(B), the ultrasonic body tissue detecting device of this embodiment may set the arrayed direction of the frequency components with high values (intensity) as a v'-direction, and the direction perpendicular to the v'-direction as a u'-direction. Thus, the v'-direction may be the depth direction and the u'-direction may be the horizontal direction. The ultrasonic body tissue detecting device may determine whether the determining position is the subcutaneous tissue or the muscular tissue based on a difference between a frequency component characteristic in the v'-direction and the frequency component characteristic in the u'-direction.

Figure 7:
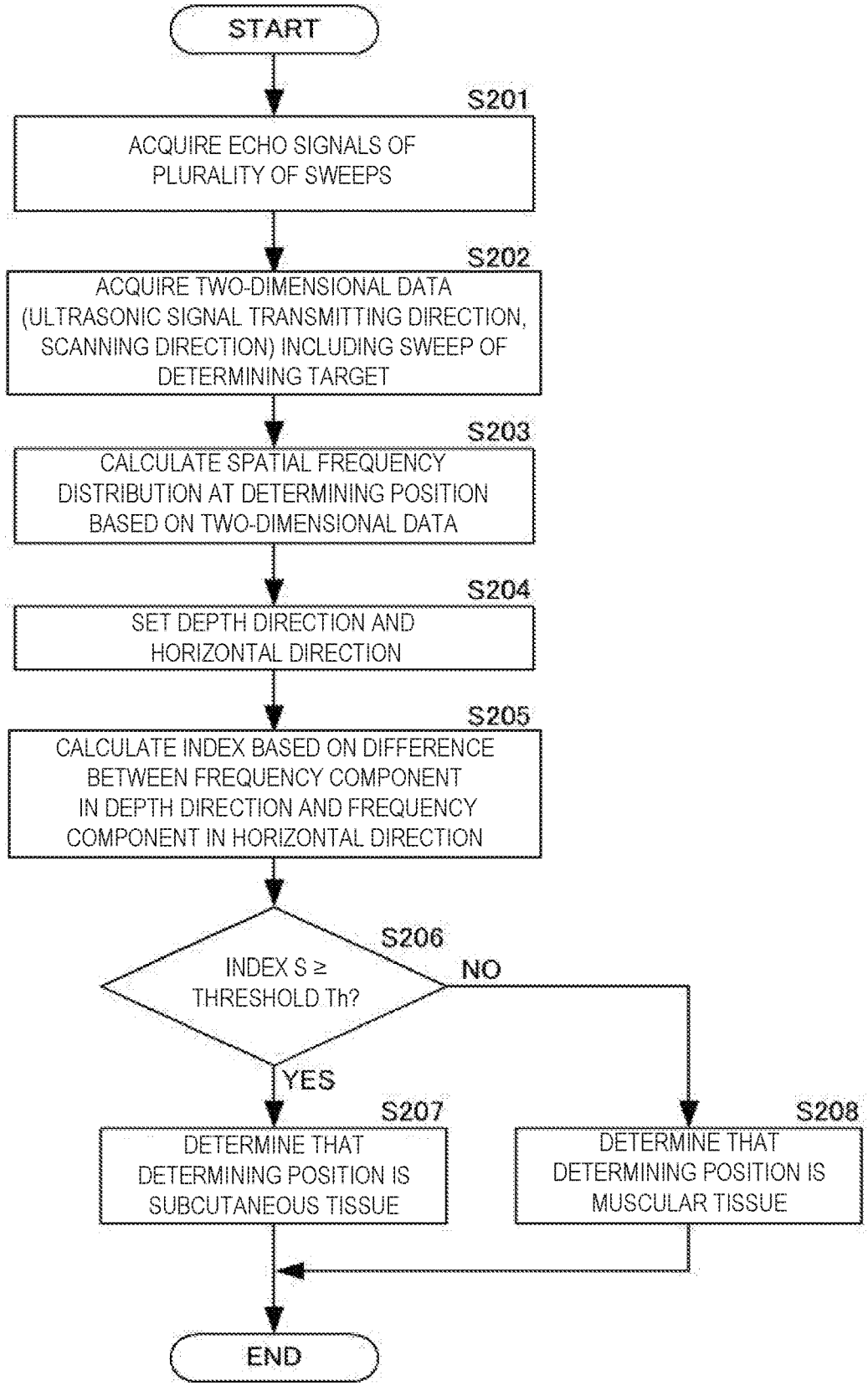
FIG. 7 is a flowchart illustrating a processing flow of a method of ultrasonically detecting body tissue according to a second embodiment of the present disclosure.

For example, determination processing may be performed using the following flow. FIG. 7 is a flowchart illustrating the processing flow of a method of ultrasonically detecting the body tissue according to the second embodiment of the present disclosure.

The arithmetic processing device may acquire the echo signals of the plurality of sweeps (S201).

The arithmetic processing device may acquire the two-dimensional data (defined two-dimensionally into the ultrasonic wave transmitting direction and the scanning direction) including the determining position using the echo signals of the plurality of sweeps (S202). Note that the arithmetic processing device may further form two-dimensional echo image data based on the two-dimensional data.

The arithmetic processing device may calculate the spatial frequency distribution at the determining position using the two-dimensional data (S203).

The arithmetic processing device may detect a direction in which the frequency component is continuously high over a broad band of frequency using the spatial frequency distribution, and set the direction as the depth direction (v'-direction). As the spatial frequency distribution used for this processing, a distribution at a position near the skin surface may be used. For example, echo signals with short periods of time passed from the transmitting timing of the ultrasonic signal may be selected. The arithmetic processing device may set the direction perpendicular to the depth direction (v'-direction) as the horizontal direction (u'-direction) (S204).

The arithmetic processing device may calculate the index S based on a difference between the frequency component in the depth direction (v'-direction) and the frequency component in the horizontal direction (u'-direction) in the spatial frequency distribution (S205).

If the index S is above the threshold Th (S206: YES), the arithmetic processing device may determine that the determining position is the subcutaneous tissue (S207). If the index S is below the threshold Th (S206: NO), the arithmetic processing device may determine that the determining position is the muscular tissue (S208).

By using such a configuration, the determining position may be automatically detectable whether it is the subcutaneous tissue or the muscular tissue, certainly and with high precision, even if the transmitting direction of the ultrasonic signal is not parallel to the depth direction. Moreover, this embodiment may be also automatically detectable of the body tissue to be detected certainly and with high precision, similar to the first embodiment.

Note that, although not illustrated in each embodiment described above, a concrete method of distinguishing the skin surface and the femur surface separately from the subcutaneous tissue and the muscular tissue may be, for example, set as follows.

The skin surface and the femur surface may have features in a luminosity distribution (a characteristic of a frequency component distribution) which are completely different from the subcutaneous tissue and the muscular tissue, and have features at positions in the transmitting direction of the ultrasonic signal. Therefore, the skin surface and the femur surface may be separable from the subcutaneous tissue and the muscular tissue based on these features.

For example, a continuity of the line part in the scanning direction may be quantized, and the numeral may be then compared with a threshold. Moreover, for example, a line part nearest to the probe 100 in the ultrasonic wave transmitting direction may be detected as the skin surface, and the furthest line part may be detected as the femur surface.

Moreover, in the embodiment described above, the mode is illustrated in which the determination may be performed using the integrated value of the difference values between the v-direction frequency component characteristic and the u-direction frequency component characteristic, or the difference value between the v'-direction frequency component characteristic and the u'-direction frequency component characteristic. However, the determination may be performed only based on a difference value between the v-direction frequency component characteristic and the u-direction frequency component characteristic at a position away from the reference point by a given frequency distance, or a difference value between the v'-direction frequency component characteristic and the u'-direction frequency component characteristic. In this case, a position of the frequency which is as high as possible may be set.

The invention claimed is:

1. An ultrasonic body tissue detecting device, comprising:
   a transceiver configured to transmit an ultrasonic signal into a body of a sample and to receive an echo signal of the ultrasonic signal; and
   processing circuitry configured to:
      acquire two-dimensional data in a transmitting direction of the ultrasonic signal and in a scanning direction perpendicular to the transmitting direction of the ultrasonic signal based on echo signals acquired at a plurality of positions along a surface of the sample;
      form two-dimensional echo image data using the two-dimensional data;
      perform a spatial frequency conversion of the two-dimensional echo image data two-dimensionally into a depth direction defined by the transmitting direction of the ultrasonic signal and into a horizontal direction perpendicular to the depth direction;
      for each of a plurality of determining positions, calculate a spatial frequency distribution based on the two-dimensional data centering on the determining position; and
      determine whether each of the determining positions is muscular tissue or subcutaneous tissue based at least in part on a difference between a distribution of a frequency component in the depth direction and a distribution of a frequency component in the horizontal direction of the spatial frequency distribution, wherein the difference is a difference between the frequency components at two points of which a spatial frequency in the depth direction is identical to a spatial frequency in the horizontal direction in the spatial frequency distribution.

2. The ultrasonic body tissue detecting device of claim 1, wherein the processing circuitry is further configured to determine whether each of the determining positions is muscular tissue or subcutaneous tissue based at least in part on an integrated value obtained by integrating the difference between the frequency components at the two points in the depth direction and the horizontal direction.

3. The ultrasonic body tissue detecting device of claim 2, wherein the processing circuitry is further configured to whether each of the determining positions is muscular tissue or subcutaneous tissue based at least in part on a result of comparison of the integrated value with a given threshold.

4. The ultrasonic body tissue detecting device of claim 3, wherein the processing circuitry is further configured to determine that each of the determining positions is the muscular tissue if the integrated value is below the threshold.

5. The ultrasonic body tissue detecting device of claim 1, wherein, the processing circuitry is further configured to:
   detect an angle difference between the transmitting direction of the ultrasonic signal and the depth direction using the spatial frequency distribution, and
   calculate a distribution of amplitude in the depth direction and a distribution of the amplitude in the horizontal direction based on the angle difference.

6. A method of ultrasonically detecting body tissue, comprising:
   transmitting an ultrasonic signal into a body of a sample and receiving an echo signal of the ultrasonic signal;
   acquiring two-dimensional data in a transmitting direction of the ultrasonic signal and in a scanning direction perpendicular to the transmitting direction of the ultrasonic signal based on echo signals acquired at a plurality of positions along a surface of the sample;
   forming two-dimensional echo image data using the two-dimensional data; performing a spatial frequency conversion of the two-dimensional echo image data two-dimensionally into a depth direction defined by the transmitting direction of the ultrasonic signal and into a horizontal direction perpendicular to the depth direction;
   for each of a plurality of determining positions, calculating a spatial frequency distribution based on the two-dimensional data centering on the determining position; and
   determining whether each of the determining positions is muscular tissue or subcutaneous tissue based at least in part on a difference between a distribution of a frequency component in the depth direction and a distribution of a frequency component in the horizontal direction of the spatial frequency distribution, wherein the difference is a difference between the frequency components at two points of which a spatial frequency in the depth direction is identical to a spatial frequency in the horizontal direction in the spatial frequency distribution.

7. The method of claim 6, wherein the determining whether each of the determining positions is muscular tissue or subcutaneous tissue includes:
   detecting an angle difference between the transmitting direction of the ultrasonic signal and the depth direction using the spatial frequency distribution; and
   calculating the distribution of the frequency component in the depth direction and the distribution of the frequency component in the horizontal direction based on the angle difference.

8. A non-transitory computer readable medium storing an ultrasonic body tissue detecting program configured to cause a computer to execute processing to determine body tissue to be detected based on an echo signal acquired by transmitting an ultrasonic signal into a body of a sample, the computer, when executing the ultrasonic body tissue detecting program of the non-transitory computer readable medium, being caused to:
   acquire two-dimensional data in a transmitting direction of the ultrasonic signal and in a scanning direction perpendicular to the transmitting direction of the ultrasonic signal based on echo signals acquired at a plurality of positions along a surface of the sample;
   form two-dimensional echo image data using the two-dimensional data;
   perform a spatial frequency conversion of the two-dimensional echo image data two- dimensionally into a depth direction defined by the transmitting direction of the ultrasonic signal and into a horizontal direction perpendicular to the depth direction;

for each of a plurality of determining positions, calculate a spatial frequency distribution based on the two-dimensional data centering on the determining position; and determine whether each of the determining positions is muscular tissue or subcutaneous tissue based at least in part on a difference between a distribution of a frequency component in the depth direction and a distribution of a frequency component in the horizontal direction of the spatial frequency distribution, wherein the difference is a difference between the frequency components at two points of which a spatial frequency in the depth direction is identical to a spatial frequency in the horizontal direction in the spatial frequency distribution.

9. The non-transitory computer readable medium of claim 8, wherein the computer is further caused to, as the determining whether each of the determining positions is muscular tissue or subcutaneous tissue:

detect an angle difference between the transmitting direction of the ultrasonic signal and the depth direction using the spatial frequency distribution; and calculate the distribution of the frequency component in the depth direction and the distribution of the frequency component in the horizontal direction based on the angle difference.

10. The ultrasonic body tissue detecting device of claim 1, wherein the processing circuitry is further configured to:

detect an angle difference between the transmitting direction of the ultrasonic signal and the depth direction using the spatial frequency distribution, and calculate a distribution of amplitude in the depth direction and a distribution of the amplitude in the horizontal direction based on the angle difference.

11. The ultrasonic body tissue detecting device of claim 2, wherein the processing circuitry is further configured to:

detect an angle difference between the transmitting direction of the ultrasonic signal and the depth direction using the spatial frequency distribution, and calculate a distribution of amplitude in the depth direction and a distribution of the amplitude in the horizontal direction based on the angle difference.

12. The ultrasonic body tissue detecting device of claim 3, wherein the processing circuitry is further configured to:

detect an angle difference between the transmitting direction of the ultrasonic signal and the depth direction using the spatial frequency distribution, and calculate a distribution of amplitude in the depth direction and a distribution of the amplitude in the horizontal direction based on the angle difference.

13. The ultrasonic body tissue detecting device of claim 4, wherein the processing circuitry is further configured to:

detect an angle difference between the transmitting direction of the ultrasonic signal and the depth direction using the spatial frequency distribution, and calculate a distribution of amplitude in the depth direction and a distribution of the amplitude in the horizontal direction based on the angle difference.

14. The ultrasonic body tissue detecting device of claim 1, wherein the surface of the sample comprises a skin surface, and wherein the horizontal direction is parallel to the skin surface.

* * * * *